US008222032B2

(12) United States Patent
Parker et al.

(10) Patent No.: US 8,222,032 B2
(45) Date of Patent: Jul. 17, 2012

(54) CELL LINES AND METHODS FOR PRODUCING PROTEINS

(75) Inventors: Stephen H. Parker, Jefferson, GA (US); Yashwant M. Deo, New Brunswick, NJ (US)

(73) Assignee: Synageva BioPharma Corp., Lexington, MA (US)

( * ) Notice: Subject to any disclaimer, the term of this patent is extended or adjusted under 35 U.S.C. 154(b) by 0 days.

(21) Appl. No.: 12/455,736

(22) Filed: Jun. 5, 2009

(65) Prior Publication Data

US 2009/0253176 A1 Oct. 8, 2009

Related U.S. Application Data

(62) Division of application No. 10/960,169, filed on Oct. 7, 2004, now abandoned.

(60) Provisional application No. 60/509,353, filed on Oct. 7, 2003.

(51) Int. Cl.
| | |
|---|---|
| *C12N 5/00* | (2006.01) |
| *C12N 5/10* | (2006.01) |
| *C12N 5/09* | (2010.01) |
| *C12N 15/00* | (2006.01) |
| *C12N 15/11* | (2006.01) |
| *C12N 15/87* | (2006.01) |

(52) U.S. Cl. .......... 435/349; 435/383; 435/325; 800/19; 536/23.1; 536/232

(58) Field of Classification Search ........................ None
See application file for complete search history.

(56) References Cited

U.S. PATENT DOCUMENTS

| | | | |
|---|---|---|---|
| 4,997,763 | A | 3/1991 | Hughes et al. |
| 5,011,780 | A | 4/1991 | Perry |
| 5,162,215 | A | 11/1992 | Bosselman et al. |
| 5,340,740 | A | 8/1994 | Petitte et al. |
| 5,656,479 | A | 8/1997 | Petitte et al. |
| 6,027,722 | A | 2/2000 | Hodgson |
| 6,730,822 | B1 | 5/2004 | Ivarie |
| 7,176,300 | B2 | 2/2007 | Rapp |
| 2002/0108132 | A1 | 8/2002 | Rapp |
| 2002/0116732 | A1 | 8/2002 | Christmann |
| 2003/0008288 | A1 | 1/2003 | Germino et al. |
| 2003/0126629 | A1 | 7/2003 | Rapp et al. |
| 2004/0019923 | A1 | 1/2004 | Ivarie et al. |
| 2005/0227315 | A1 | 10/2005 | Pain et al. |
| 2006/0130170 | A1 | 6/2006 | Leavitt et al. |

FOREIGN PATENT DOCUMENTS

| | | |
|---|---|---|
| WO | WO 90/11355 | 10/1990 |
| WO | WO 97/47739 | 12/1997 |
| WO | WO 99/10505 | 3/1999 |
| WO | WO 02/16620 | 2/2002 |

OTHER PUBLICATIONS

Kawabe et al, Development of Oviduct-Specific Gene Expression System for Transgenic Avian Bioreactor, 2003, M. Kamihira et al. (eds.), Animal Cell Technology: Basic & Applied Aspects, Animal Cell Technology: Basic & Applied Aspects 16, pp. 203-208.*
Fredrickson et al, Ovarian Tumors of the Hen, Environmental Health Perspectives, 1987, vol. 73, pp. 35-51.*
Palmiter, Richard D.; Regulation of Protein Synthesis in Chick Oviduct, *The Journal of Biological Chemistry* 1972; 24: (20) 6450-6461.
Yu, et al.; Development, Cellular Growth, and Function of the Avian Oviduct, *Biology of Reproduction*, 1973; 8:283-298.
Mulvihill, et al.; Relationship of Nuclear Estrogen Receptor Levels to Induction of Ovalbumin and Conalbumin mRNA in Chick Oviduct, *The Journal of Biological Chemistry*, 1977; 252: (6) 2060-2068.
McKnight, et al.; Transcriptional Regulation of the Ovalbumin and Conalbumin Genes by Steroid Hormones in Chick Oviduct, *The Journal of Biological Chemistry*, 1979; 254: (18) 9050-9058.
Mulvihill, et al.; Revelation of Nuclear Progesterone Receptors to Induction of Ovalbumin and Conalbumin mRNA in Chick Oviduct, *The Journal of Biological Chemistry*, 1980; 255: (5) 2085-2091.
Shepherd, et al.; Commitment of Chick Oviduct Tubular Gland Cells to Produce Ovalbumin mRNA during Hormonal Withdrawal and Restimulation, *The Journal of Cell Biology*, 1980; 87: 142-151.
Palmiter, et al.; Steroid Hormone Regulation of Ovalbumin and Conalbumin Gene Transcription, *The Journal of Biological Chemistry*, 1981; 256: (15) 7910-7916.
Sanders, et al.; Chicken Egg White Genes: Multihormonal Regulation in a Primary Cell Culture System, *Endocrinology*, 1985; 116: (1) 398-405.
Tsai, et al.; Effect of Estrogen on Gene Expression in the Chick Oviduct. Regulation of the Ovomucoid Gene, *Biochemistry*, 1978; 17: (26) 5773-5790.
Hynes, et al.; mRNA Complexity and Egg White Protein mRNA Content in Mature and Hormone-Withdrawn Oviduct, *Cell*, 1977; 11: 923-932.
Rapp, et al.; Biologically active human interferon α-2b produced in the egg white of transgenic hens, *Transgenic Research*, 2003; 12: 569-575.
Martin, et al; Differentiation of Clonal Lines of Teratocarcinoma Cells: Formation of Embryoid Bodies In Vitro,*Proc. Nat. Acad. Sci. USA*, 1975; 72: (4) 1441-1445.
Barnes, et al.; Reproductive Tract Tumors in Mature Laying Hens, Presented at AAAP/AVMA Scientific Program, Boston, MA Jul. 2001.
Hayashi, et al.; Purification and Characterization of a Neurite Outgrowth Factor from Chicken Gizzard Smooth Muscle, *The Journal of Biological Chemistry*, 1985; 260: (26) 14269-14278.
Evans, C W; Cell adhesion and metastasis, *Cell Biol. Int. Rep.*, 1992; 16: (1) 1-10.
Takeichi M.; Cadherins in cancer: implications for invasion and metastasis, *Curr. Opin. Cell Biol.*, 1993; 5: (5) 806-811.
Schimke, et al.; Hormonal regulation of ovalbumin synthesis in chick oviduct, *Basic Lift Sci.*, 1973; 1: 123-135.

(Continued)

*Primary Examiner* — Maria Marvich
(74) *Attorney, Agent, or Firm* — Hak J. Chang; Eugene J. Kim

(57) ABSTRACT

The methods of the present invention involve the manipulation and/or propagation of oviduct tumor cells derived from either wild-type or transgenic avians.

13 Claims, No Drawings

OTHER PUBLICATIONS

Kawaguchi, et al.; Establishment and Characterization of a Chicken Hepatocellular Carcinoma Cell Line, LMH, *Cancer Research*, 1987; 47: 4460-4464.

Kolluri, et al, Heme biosynthesis in a chicken hepatoma cell line (LMH): Comparison with primary chick embryo liver cells (CELC) et Biophysica Acta 1472, 1999, 658-667.

Haflon et al, Targeted gene expression without a tissue-specific promoter creating mosaic embryos using laser-induced single-cell heat shock, Proc. Natl. Acad. Sci. USA 1997, vol. 94, pp. 6255-6260.

Wynford-Thomas Conditional Immortalization of human thyroid epithelial cells: A tool for analysis of oncogene action, Mol Cell Biol. 1990, 10(10); 5365-5377.

\* cited by examiner

CELL LINES AND METHODS FOR PRODUCING PROTEINS

RELATED APPLICATION INFORMATION

This application is a Divisional of U.S. patent application Ser. No. 10/960,169, filed Oct. 7, 2004, now abandoned, the disclosure of which is incorporated in its entirety herein by reference, which claims the benefit of U.S. provisional application 60/509,353, filed Oct. 7, 2003.

BACKGROUND OF THE INVENTION

Recent advances have allowed for the generation of transgenic avians that express heterologous proteins in their oviduct cells. The avian oviduct contains an infundibulum, magnum, isthmus, shell gland, vagina and cloaca (Etches, Reproduction in Poultry. 1996, New York, N.Y.: CABI Publishing. 318). An ovulated ovum enters the tract through the infundibulum and continues to the magnum where the majority of egg white proteins, such as ovalbumin, ovomucoid and lysozyme, are produced by tubular gland cells and deposited on the ova. (Palmiter, J Biol Chem, 1972. 247: 6450-61; Yu and Marquardt, Biol Reprod, 1973. 8:283-98). Expression of the major egg white proteins is controlled by hormone responsive elements of the respective promoters (Palmiter, J Biol Chem, 1972. 247:6450-61; Schimke et al., Basic Life Sci, 1973. 1:123-35; Mulvihill and Palmiter, J Biol Chem, 1977. 252: 2060-8; McKnight and Palmiter, J Biol Chem, 1979. 254:9050-8; Mulvihill and Palmiter, J Biol Chem, 1980. 255:2085-91; Shepherd et al., J Cell Biol, 1980. 87: 142-51; Palmiter et al., J Biol Chem, 1981. 256: 7910-6; Sanders and McKnight, Endocrinology, 1985. 116: 398-405).

Chicken oviduct cells, when stimulated by steroid hormones during egg-laying, secrete three principal polypeptides, ovalbumin, ovomucoid and lysozyme (Tsai et al., (1978) Biochemistry 17: 5773-5779). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells. (Hynes et al. (1977) pp 932). The ability of the avian oviduct to express large amounts of various proteins makes it an attractive target for producing heterologous proteins. To date, the most common method of expressing heterologous proteins in avian oviducts is through the production of transgenic hens. In one example, transgenic hens expressing human Interferon alpha-2b (hIFN α2b) were generated (Rapp et al., Transgenic Research, 2003). Also, transgenic hens were generated that express human monoclonal antibody in their egg white. U.S. Pat. No. 6,730,822, issued May 5, 2004, and U.S. patent application Ser. No. 10/463,980, filed Jun. 17, 2003 filed internationally as PCT/US04/01833, U.S. patent application Ser. No. 09/877,374, filed Jun. 8, 2001 filed internationally as PCT/US02/02454, U.S. patent application Ser. No. 10/679,034, filed Oct. 2, 2003 filed internationally as PCT/US02/29878, and U.S. patent application 10/856,218, filed May 28, 2004 filed internationally as PCT/US04/16827 disclose methods and compositions useful for the generation of transgenic avians for production of heterologous proteins. The disclosure of this issued US patent and these four pending patent applications and their corresponding PCT applications are incorporated herein by reference.

Primary cultures of oviduct tissue can be generated by removing the magnum section of a sexually mature hen treated with estrogen (Sanders and McKnight, Endocrinology, 1985. 116: 398-405). The tissue is digested with collagenase and dispase to liberate small cell clumps that are cultured for short durations. Cells collected and cultured in this manner typically die or differentiate into cells that do not produce egg white protein within three days making primary cultures of normal oviduct cells unsuitable for use in large scale in vitro production of heterologous proteins. Accordingly, improved methods for producing heterologous proteins in avian oviduct cells are needed.

SUMMARY OF THE INVENTION

The present invention is based, at least in part, on the generation of avian cell lines, such as immortal avian cell lines, that can be passaged multiple times in cell culture and provide sustained production of heterologous polypeptides. In one embodiment, the methods of the present invention rely upon the manipulation and/or propagation of oviduct tumor cells derived from either wild-type or transgenic avians.

Accordingly, in one aspect, the present invention features an isolated avian cell line comprising a nucleic acid encoding a heterologous protein, wherein the cell line is sustainable in culture for at least 3 or more passages. Typically, the cell line is sustainable in culture for at least 5 passages or 10 passages or 15 passages or 20 passages or 25 passages or 30 passages or 35 passages or 40 passages or 45 passages or 50 passages or 500 passages or 1000 passages or 5000 passages. In a particularly useful embodiment, the cell line is an immortal cell line capable of an unlimited number of passages. The nucleic acid is typically operably linked to an oviduct-specific promoter or a non-specific promoter capable of controlling expression of the nucleic acid.

Suitable oviduct-specific promoters include, for example, and without limitation, ovomucoid promoters, ovalbumin promoters, and lysozyme promoters, conalbumin promoters, ovomucin promoters, ovotransferrin promoters and functional portions of each of these promoters. Suitable non-specific promoters include, for example and without limitation, cytomegalovirus (CMV) promoters, MDOT promoters and rous-sarcoma virus (RSV) promoters, murine leukemia virus (MLV) promoters, mouse mammary tumor virus (MMTV) promoters and SV40 promoters and functional portions of each of these promoters. Nonlimiting examples of other promoters which may be useful in the present invention include, without limitation, Pol III promoters (for example, type 1, type 2 and type 3 Pol III promoters) such as H1 promoters, U6 promoters, tRNA promoters, RNase MPR promoters and functional portions of each of these promoters. Typically, functional terminator sequences are selected for use in the present invention in accordance with the promoter that is employed.

Avian oviduct cell lines as disclosed herein are contemplated as being derived from any suitable avian source including, but not limited to, chicken, turkey, duck, goose, quail, pheasant, parrot, finch, hawk, crow or ratite, for example, ostrich, emu, cassowary. In one useful embodiment, the cell line is derived from a chicken. In one embodiment, the cell line is isolated from a wild type or transgenic avian that expresses the heterologous protein in oviduct cells. In one embodiment, the tumor cell line is contemplated as being derived from certain oviduct tumors, such as an epithelial or mesenchymal tumors, which include, for example, adenocarcinomas, mesenchymal adenomas, leiomyomas, and fibromas. In particularly useful embodiment, the cell line is derived from epithelial adenomas tumors.

The present invention further features a composition comprising the isolated avian oviduct cell line of the invention within a culture medium. In a related embodiment, the culture medium comprises a heterologous protein expressed by the cell line.

The present invention also features a method of producing a heterologous protein comprising contacting an avian oviduct tumor cell with a nucleic acid encoding a heterologous protein under conditions suitable for expression of the protein, wherein the tumor cell is sustainable in culture for at least 3, for example, 5, 10 passages, 15 passages, 20 passages, 50 passages or more passages, and then isolating the heterologous protein. The nucleic acid can be transfected into the cell in vitro, for example, by microinjection, electroporation or lipofection or may be transfected into the cell in vivo. The nucleic acid can further include a selectable marker to facilitate selection of tumor cells that express the marker. In an additional related embodiment, the method includes enriching for tumor cells that express the heterologous protein, by, for example, selecting for tumor cells that express gicerin (for example, using a fluorescently labeled antibody that binds gicerin) or selecting for tumor cells that bind neurite outgrowth factor (NOF).

The present invention also features a method of producing a heterologous protein comprising isolating oviduct tumor cells that express the protein. In one embodiment, the cell is sustainable in culture for at least 3 or more passages, culturing the tumor cells under conditions suitable for expression of the protein, and then isolating the protein.

The invention also provides heterologous proteins that are produced by the foregoing methods and cell lines. Such proteins can include, for example, antibodies, cytokines, fusion proteins, growth factors, enzymes, structural proteins, interferons, granulocyte-colony stimulating factor, and erythropoietins. Pharmaceutical compositions comprising the heterologous proteins along with a pharmaceutically acceptable carrier also are provided.

Any combination of features described herein is included within the scope of the present invention provided that the features included in any such combination are not mutually inconsistent. Such combinations will be apparent based on this specification and the knowledge of one of ordinary skill in the art.

DETAILED DESCRIPTION

The present invention relates to the isolation and enrichment of avian oviduct cells to obtain sustainable cell lines that can be passaged multiple times in cell culture and can be used for long-term production of heterologous polypeptides at higher yields. The methods of the present invention involve the manipulation and/or propagation of oviduct tumor cells derived from either wild-type or transgenic avians. The tumor cells may be isolated directly from the wild-type or transgenic avians or may be obtained by genetically altering (for example, by mutagenesis) cells taken from normal oviduct tissue of wild-type or transgenic avians. Preferably, the transgenic avians produce heterologous protein in oviduct cells.

For purposes of describing the invention, the following terms and definitions may be used.

The term "isolated avian oviduct tumor cell" and "avian oviduct tumor cell" or "oviduct tumor cell" as used herein, refers to a cell substantially free of other cell types found in tumors or non-tumorous avian oviduct tissue. An avian oviduct tumor cell line as disclosed herein, may refer to cell lines obtained from one or more cells of avian oviduct tumors or cell lines obtained from one or more cells which have been subjected to in vitro mutagenesis as disclosed herein.

The term "sustainable", as used herein, refers to the ability of the cell or cell line to be passaged in culture for at least three or more, or ten or more times, preferably twenty or more or an infinite number of times.

The term "transfected", as used herein, refers to the uptake of heterologous DNA or RNA by a cell. Transfection, as used herein, encompasses all art-recognized procedures for introducing nucleic acid into cells, including, for example, microinjection, electroporation, chemical transfection and transduction into a cell.

The term "oviduct tumor", as used herein, refers to tumorous tubular gland cells from an avian oviduct (typically the magnum) that secretes egg white proteins including, for example, ovalbumin, ovomucoid, ovoinhibitor, conalbumin, ovomucin and lysozyme. Avian oviduct tumors are typically of an epithelial or mesenchymal nature. Epithelial tumors usually consist of adenomas or adenocarcinomas. Mesenchymal tumors typically consist of adenomas, leiomyomas or fibromas.

As used herein the terms "polypeptide" and "protein" refer to a polymer of amino acids, linked through peptide bonds. The term "polypeptide" includes proteins, protein fragments, protein analogues, oligopeptides and the like. The term polypeptide as used herein can also refer to a peptide.

The term "heterologous protein", as used herein, refers to a protein that is not naturally expressed by the cell that produces the protein.

The term "avian" as used herein refers to any species, subspecies or race of organism of the taxonomic class ava, such as chicken, turkey, duck, goose, quail, pheasants, parrots, finches, hawks, crows and ratites. The term includes the various known strains of *Gallus gallus*, or chickens, for example, White Leghorn, Brown Leghorn, Barred-Rock, Sussex, New Hampshire, Rhode Island, Ausstralorp, Minorca, Amrox, California Gray, Italian Partidge-colored, as well as strains of turkeys, pheasants, quails, duck, ostriches and other poultry commonly bred in commercial quantities.

The terms "nucleic acid" and "polynucleotide", as used herein refer to any natural or synthetic array of nucleotides (or nucleosides), for example cDNA, genomic DNA, mRNA, tRNA, oligonucleotides, oligonucleosides and derivatives thereof. The term "gene" as used herein refers to a nucleic acid or polynucleotide (including both RNA or DNA) that encodes genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". Such genes may be contained in an "expression vector" which, as used herein, refers to a nucleic acid vector that comprises an expression control region operably linked to a nucleotide sequence coding for at least one polypeptide. Such expression vectors therefore drive transcription and expression of the gene.

As used herein, the term "regulatory sequences" includes promoters, enhancers, and other elements that may control gene expression. Standard molecular biology textbooks such as Sambrook et al. eds "Molecular Cloning: A Laboratory Manual" 3rd ed., Cold Spring Harbor Press (2001) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed. Representative examples of expression vectors include, for example, bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like and vectors derived from bacteriophage nucleic acid, for example, plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. Accordingly, the term "nucleic acid vector" or "vector" as used herein refers to a natural or synthetic single or double stranded plasmid or viral nucleic acid molecule, or any other nucleic acid molecule that can be transfected or transformed into cells and replicate independently of, or within, the host cell genome. A nucleic acid can be inserted into a vector by cutting the vector with restriction enzymes and ligating the pieces together. The nucleic acid molecule can be RNA or DNA.

The term "heterologous polypeptide", as used herein, refers to a polypeptide that does not naturally occur in a host cell.

The term "expressed" or "expression" as used herein refers to the transcription of a nucleotide sequence into an RNA nucleic acid molecule at least complementary in part to a region of one of the two nucleic acid strands of a gene coding sequence and/or to the translation from an RNA nucleic acid molecule into a protein or polypeptide.

The term "operably linked" as used herein refers to the configuration of coding and control sequences, for example, within an expression vector, so as to achieve transcription and/or expression of the coding sequence. Thus, control sequences operably linked to a coding sequence are capable of effecting the expression of the coding sequence and regulating in which tissues, at what developmental time points, or in response to which signals, and the like, a gene is expressed. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated or transcribed sequences can be present between a promoter sequence and the coding sequence and the promoter sequence can still be considered "operably linked" to the coding sequence. Such intervening sequences include but are not limited to enhancer sequences which are not transcribed or are not bound by polymerase.

The terms "gene expression control regions" or "gene expression controlling regions" as used herein refer to nucleotide sequences that are associated with a nucleic acid sequence and which regulate, in whole or in part, the expression of the nucleic acid sequence, for example, regulate in whole or in part the transcription of a nucleotide sequence.

The term "oviduct-specific promoter", as used herein, refers to a promoter from a gene specifically expressed in avian oviduct cells including, but not limited to, promoters from ovalbumin, lysozyme, conalbumin, ovomucoid or ovotransferrin genes.

The terms "transformation" and "transfection" as used herein refer to the process of inserting a nucleic acid into a host cell. Many techniques are well known to those skilled in the art to facilitate transformation or transfection of a nucleic acid into a prokaryotic or eukaryotic cell. These methods include a variety of techniques, which may include, but are not limited to, viral transduction, microinjection, treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration. Other transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents. Certain methods useful for the introduction of nucleic acid into a cell are disclosed in, for example, U.S. patent application Ser. No. 09/919,143, filed Jul. 31, 2001 and U.S. patent application Ser. No. 10/811,136, filed Mar. 26, 2004. The disclosure of each of these two patent applications is incorporated in its entirety herein by reference.

The term "enriched", as used herein with respect to avian oviduct-specific tumor cells, refers to an increase in the number of such cells relative to the total cell population in which they are contained (i.e., an increase in the number of tumor cells relative to the number of non-tumor cells).

As used herein, a "transgenic avian" includes an avian, for example, a chicken, turkey, duck, goose, quail, pheasant, parrot, finch, hawk, crow or ratite, for example, ostrich, emu, cassowary, in which one or more, for example, essentially all of the cells of the avian include a transgene. The transgene is introduced into the cell, directly or indirectly by introduction into a precursor of the cell, for example, by microinjection, transfection or infection, for example, by infection with a recombinant virus. The term genetic manipulation includes the introduction of a recombinant DNA molecule. This molecule may be integrated within a chromosome, or it may be extrachromosomally replicating DNA.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "transgenic cell" refers to a cell containing a transgene.

As used herein, the term "marker sequence" refers to a nucleic acid molecule that is used to identify those cells that have incorporated the targeting construct into their genome. For example, the marker sequence can be a sequence encoding a protein which confers a detectable trait on the cell, such as an antibiotic resistance gene, for example, neomycin resistance gene, or an assayable enzyme not typically found in the cell, for example, alkaline phosphatase, horseradish peroxidase, luciferase, beta-galactosidase and the like.

As used herein, a "naturally-occurring" nucleic acid molecule refers to an RNA or DNA molecule having a nucleotide sequence that occurs in an organism found in nature.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be a mammalian cell, for example, a human cell. In certain embodiments, the host cell is an epithelial cell, for example, a pancreatic epithelial cell.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (for example, it is inserted at a location that differs from that of the natural gene or its insertion results in a knockout). A trangene also includes a regulatory sequence designed to be inserted into the genome such that it regulates the expression of an endogenous coding sequence, for example, to increase expression and/or to change the timing and or tissue specificity of expression, for example, to effect "gene activation".

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')$_2$ fragments, disulfide-linked Fvs (sdFv) fragments, for example, as produced by a Fab expression library, anti-idiotypic (anti-Id) antibodies, intrabodies, synthetic antibodies, and epitope-binding fragments of any of the above.

The techniques used to isolate and characterize nucleic acids and proteins according to the methods of the present invention are well known to those of skill in the art and standard molecular biology and biochemical manuals may be consulted to select suitable protocols without undue experimentation. See, for example, Sambrook et al. (2001) Molecular Cloning: A Laboratory Manual, 3rd ed., Cold Spring Harbor Press, the content of which is herein incorporated by reference in its entirety.

Some abbreviations used in the present specification include the following: aa, amino acid(s); bp, base pair(s); cDNA, DNA complementary to RNA; min, miunte(s); nt, nucleotide(s); SSC, sodium chloride-sodium citrate; UTR, untranslated region; DMSO, dimethyl sulfoxide; ul, microliter; and uM; micromolar.

Various aspects of the invention are described in further detail in the following.

The present invention relates to avian oviduct cell lines which are capable of producing heterologous proteins. In a particularly useful embodiment, the cell lines are immortal. That is, the cells are capable of undergoing an indefinite number of cell divisions.

Cell lines of the present invention may be obtained using any useful method. In one embodiment, the tumor cell lines are derived or obtained from avians having tumors in their reproductive organs, in particular, the oviduct. It has been determined that avians, such as chickens, will spontaneously produce tumors in the oviduct and that such tumors become more prevalent as the avian ages. For example, it is believed that more than half of the domestic chickens over the age of five years have such tumors. In addition, the tumors can be induced in avians using mutagens or carcinogens as is understood in the field of mutation research. In one particularly useful embodiment, the avian tumors arise from one or more tubular gland cells.

Examples of carcinogens and mutagens contemplated for use in producing avian oviduct tumors include, without limitation, acrylonitrile, adriamycin, aflatoxins, arsenic and arsenic compounds, asbestos, benzene, benzidine n,n-bis (2-chloroethyl)-2-naphthylamine, benzo (a) pyrene, beryllium and beryllium compounds, bis(chloromethyl) ether, 1,4-butanediol, cadmium and cadium compounds, carbon tetrachloride, chloroform, chromium and chromium compounds, chloromethyl methyl ether, conjugated estrogens, 2,4-diaminotoluene, 1,2-dibromo-3-chloropropane, dichloroethane, ddt, diethylstilbestrol, diethylsulfate, 1,4-dioxane, ethylene dibromide (edb), ethylene oxide, ethylene thiourea, ethyl methanesulfonate, formaldehye (formalin solutions), hydrazine and hydrazine sulfate, lead acetate and lead phosphate, 3-methylcholanthrene, methylhydrazine, methyl iodide, methylene chloride, methyl methanesulfonate, 1-methyl-3-nitro-1-nitrosoguanidine, 4,4-methylenebis(2-chloroaniline) (mboca), 2-napthylamine, nickel and nickel compounds, 4-nitrobiphenyl, nitrogen mustard, 2-nitropropane, n-nitrosodi-n-bytylamine, n-nitrosodiethyl-amine, n-nitrosodimethyl-amine, n-nitroso-n-ethylurethane, oxymetholone, phenacetin, phenytoin, polychlorinated byphenyls, procarbazine, progesterone, 1,3-propane sultone, b-propiolactone, reserpine, saccharin, safrole, selenium sulfide, 2,3,7,8-tetrachlorodibenzo-p-dioxin (tcdd), thioacetaminde, thiourea, thoriumdioxide, o-toluidine, m-troluenediamine, toxaphene, tris (1 aziridinyl) phosphine sulfide, tris(2,3-dibromopropyl) phosphate, uracil mustard, urethane and vinyl chloride.

In another embodiment, avian oviduct cells, for example, tubular gland cells, may be immortalized in vitro. Immortalization of the avian cells may be spontaneous, or may be induced by mutagens or by transfection using certain oncogenes. Mutagens, such as those disclosed for use herein for the production of avian tumors, can be employed for the in vitro production of immortal avian oviduct tumor cell lines utilizing methodologies well known to those of ordinary skill in the art. Examples of oncogenes which may be useful for the production of immortalized cells include, without limitation, genes for: growth factors, growth factor receptors, protein kinases, signal transducers, nuclear phosphoproteins, and transcription factors. Such oncogenes may be employed by a person of ordinary skill in the field utilizing methods known in the art to produce immortal avian oviduct tumor cell lines.

Oviduct tumor cells can be isolated from tumorous avian oviducts using any suitable tissue isolation technique known in the art. For example, tumor cells can be obtained by removing and dissecting the oviduct of a female avian to expose the luminal side. The oviduct is examined and any tumors, polyps or abnormal growths are excised for processing. Avian oviduct tumors are typically of an epithelial or mesenchymal nature. Epithelial tumors usually consist of adenomas or adenocarcinomas. Mesenchymal tumors typically consist of adenomas, leiomyomas or fibromas. Once collected, the tumor can be placed in a suitable basal salt medium, such as F12, and stored on ice for up to 4 hours.

The oviduct tumor can be finely minced, for example, into 1-2 mm pieces, and incubated in a suitable media, such as F12 with collagenase (for example, 0.08-8.0 mg/ml) and dispase (for example, 0.1-10.0 mg/ml). In one embodiment, the tissue is shaken at 37-42° C. for 1 to 30 minutes, (400 rpm) and triturated to generate clumps each consisting of 100-1000 cells. Clumps of cells are allowed to settle out and the supernatant, containing red blood cells and cellular debris, is discarded. The clumps are suspended in pre-warmed F12 media, supplemented with collagenase (0.08-8.0 mg/ml) and dispase (0.1-10.0 mg/ml), and incubated at 37-42° C. with shaking (400 rpm). Clumps are triturated every ten minutes to generate clumps consisting of 5-100 cells that are subsequently pelleted with low speed centrifugation (~800 rpm). The resultant pellet is suspended in ice cold F12 and filtered through a single layer of surgical gauze tape to remove larger clumps. Cells are washed twice with ice cold F12, pelleted and suspended in the growth medium at an $OD_{600}$ of 0.3-3.0. Cells collected with this technique are suitable for use in the methods described below.

All subsequent culturing typically utilizes a basal salt media, such as F12, DMEM, MEM, and the like. supplemented with fetal calf serum, fetal bovine serum or chicken serum to 0.1%-15% total volume, 0.01-1000 nM estrogen, 1-10000 nM corticosterone and 0.01-1000 uM insulin. This medium is hereafter referred to as "growth media". Cells derived from oviduct tumors can be isolated through multiple passages in such appropriate growth media. Initially, cells isolated from the original oviduct samples are grown in growth media (for example, at 1-5% $CO_2$ and 37°-42° C.) until the culture reaches confluency or the diameter of cell clumps reaches approximately one millimeter. Cell clumps and monolayers are subsequently treated with basal salts media containing collagenase (0.08-8 mg/ml) and dispase (0.1-10 mg/ml) to produce single cell suspension. Cells are pelleted and washed twice with basal salt media. After final wash, the cell pellet is suspended in growth media at a cell density of $1 \times 10^4$-$1 \times 10^6$ cells per milliliter.

Single colony isolates of cultured cells can be isolated using limiting dilution techniques. Cultured cells are dispersed as described above. Single cells are plated in each well of 96 well plate and incubated in growth media. Alternatively single cells can be cultured on a monolayer of cells such as whole embryo fibroblasts, STO (Martin and Evans, Proc Natl Acad Sci USA, 1975. 72: 1441-5), or LMH (Kawaguchi et al., Cancer Res, 1987. 47: 4460-4). Supernatent from each well can be collected every three days and the levels of ovalbumin, ovomucoid and lysozyme determined by ELISA (ovomucoid and ovalbumin) or bioactivity assay (lysozyme). Clones that express any or all of the defined egg white proteins are passaged as needed to maintain viability.

Avian tumor cells isolated as described above can be transfected with nucleic acids, for example, transgenes, encoding a variety of heterologous proteins using techniques well known in the art, such that sustained production of the proteins is achieved. Typically, the nucleic acid is present within a suitable expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced, for example, bacterial vectors having a bacterial origin of replication and episomal mammalian vectors. Other vectors, such as non-episomal mammalian vectors, are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include other forms of expression vectors, such as viral vectors, for example, replication defective retroviruses, adenoviruses and adeno-associated viruses.

Suitable vectors for use in the present invention comprise nucleic acid sequence encoding heterologous protein(s), that are operatively linked to one or more regulatory sequences, for example, promoter sequences. The phrase "operably linked" is intended to mean that the nucleotide sequence of interest, for example, the sequence encoding the heterologous protein, is linked to the regulatory sequence(s) in a manner which allows for expression of the nucleotide sequence (for example, in an in vitro transcription/translation system or in a host cell when the vector is introduced into the host cell). The term "regulatory sequence" is intended to include promoters, enhancers and other expression control elements, for example, polyadenylation signals. Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells, for example, oviduct-specific regulatory sequences. Other elements included in the design of a particular expression vector can depend on such factors as the choice of the host cell to be transformed, the level of expression of protein desired and the like. The expression vectors of the invention can be introduced into host cells to thereby produce proteins or peptides, including fusion proteins or peptides, encoded by nucleic acids as described herein.

Vectors as described above can be introduced into isolated avian tumor cells using any of a variety of well known techniques well known in the field. Suitable methods may be described, for example, in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al., "Construction and propagation of human adenovinis vectors," in Cell Biology: A Laboratory Handbook, Ed. J. E. Celis., Academic Press. 2.sup.nd Edition, Volume 1, pp: 500-512, 1998; Hitt et al., "Techniques for human adenovirus vector construction and characterization," in Methods in Molecular Genetics, Ed. K. W. Adolph, Academic Press, Orlando, Fla., Volume 7B, pp:12-30, 1995; Hitt, et al., "Construction and propagation of human adenovirus vectors," in Cell Biology: A Laboratory Handbook," Ed. J. E. Celis. Academic Press. pp:479-490, 1994, each of which is also hereby incorporated by reference. The methods include, for example, stable or transient transfection, lipofection, electroporation and infection with recombinant viral vectors.

Isolated avian oviduct cell lines of the inventions transected or transformed as described above are also referred to herein as "recombinant host cells". The term "recombinant host cell" refers not only to the initial cell transfected, but also to the progeny or potential progeny of the cell. Because certain modifications may occur in succeeding generations due to either mutation or environmental influences, such progeny may not, in fact, be identical to the parent cell, but are still included within the scope of the term as used herein.

Selection vectors that contain, for example, oviduct-specific promoters, such as ovalbumin, ovomucoid or lysozyme promoters or other suitable non-specific promoters that drive expression of an antibiotic resistance gene such as neomycin, hydromycin or puromycin, can be transfected into avian tumor cells using the art-recognized techniques such as those described herein. Presence of the selection vector in the cell can be transient or clones that contain integrated copies of the selection vector can be selected for.

In one embodiment, the presence of the appropriate antibiotic, cells will survive if they are able to initiate transcription from the oviduct-specific promoter located on the selection vector provided. This technique therefore selects for those cells with active endogenous oviduct-specific promoters. In one useful embodiment, cells will survive if they are able to initiate transcription of an antibiotic resistance gene from the oviduct-specific promoter located on a selection vector. This technique therefore selects for those cells with active cloned oviduct-specific promoters. In one aspect of the invention, an oviduct-specific promoter drives transcription of an RNA molecule encoding both an antibiotic resistance protein product and a protein of interest such as a pharmaceutical composition. In such a case, an internal ribosome entry site may be employed between the two coding sequences.

The foregoing selection methods can be used with the initial primary cell culture or cells from subsequent passages. The cells can be continually passaged in suitable growth medium for as long as desired.

Alternatively, the selection vectors described above can drive expression of a fluorescent protein, such as Enhanced Green Fluorescence Protein (EGFP). Cells that transcribe the EGFP can then be sorted and collected using standard Florescence Assisted Cell sorting (FACS) techniques. Cells collected in this manner can be cultured and additional rounds of selection used to isolate cells with the desired egg white producing phenotype.

Metastasis of epithelial tumors often involves cell adhesion molecules (CAMs) and epithelial-extracellular matrix (ECM) proteins (Takeichi, Curr Opin Cell Biol, 1993. 5: 806-11; Evans, Cell Biol Int Rep, 1992. 16:1-10). Tsukamoto demonstrated that oviductal tumor cells bind to neurite outgrowth factor (NOF) through interactions with gicerin, a CAM expressed by cells of oviduct tumors. This interaction is evidenced by the fact that oviductal tumor cells pre-incubated with an anti-gicerin antibody exhibited decreased binding to purified and cell associated NOF. While NOF is expressed by mesentery cells of oviduct tumors, it is also expressed on chicken gizzard, skeletal muscle, heart, liver and ciliary ganglion cells (Hayashi and Miki, J Biol Chem, 1985. 260:14269-78).

The ability of oviductal tumor cells to bind NOF can be used as a tool to isolate and enrich for metastatic cells of avian oviduct tumors. Tumor cells can be collected as described earlier and placed on tissue culture plates coated with purified NOF or on a monolayer culture of avian cells prepared from the gizzard, skeletal muscle, heart, liver or ciliary ganglion, or mesenchym of an oviductal tumor. This can be done, for example, by incubating tumor cells for approx. 1 hour at 37°-41° C. at 5% $CO_2$ to allow attachment of gicerin positive cells to the purified or cell associated NOF. The cultures are washed twice with warm (37°-41° C.) DMEM to dislodge any unbound cells. Seeded cells are allowed to grow until colonies consisting of 10-1000 cells form. Colonies that arise from these cells are removed by placing a cloning cylinder around the colony and removing the culture media. The colony is then digested and liberated from the underlying NOF coated plate or NOF expressing cell monolayer using F12 containing collagenase (0.08-8 mg/ml) and dispase (0.1-10 mg/ml). The colony and its' cells are placed in an Ependorff tube and further digested with fresh F12 collagenase/dispase media. Once digestion is completed the cells are placed back into culture. This process can be repeated with the isolated colonies additional times to enrich for oviduct tumor cells. After several rounds of enrichment the cultures can be digested and single colonies from these cultures screened for production of ovalbumin, ovomucoid or lysozyme and viability after multiple passages.

Alternatively, oviduct tumor cells that express gicerin can be isolated using an anti-gicerin antibody and FACS. Cells are initially incubated with an anti-gicerin antibody. Cells are then washed to remove unbound antibody and then incubated with a detection antibody specific for the isotype of the anti-gicerin antibody. After removing unbound detection antibody, the cells that stain positive are sorted and collected using standard FACS techniques. Cells collected in this manner can be cultured and additional rounds of selection used to isolate cells with the desired heterologous protein producing phenotype. Cells and their subsequent lines should remain viable for multiple passages in a defined growth medium. The growth medium can contain, for example, supplements of fetal calf serum, fetal bovine serum or chicken serum to 0.1%-15% total volume, and 0.01-1000 nM estrogen, 1-10000 nM corticosterone and 0.01-1000 uM insulin.

In one useful embodiment of the invention, the avian cell lines originate with one or more tubular gland cells. Typically, such cell lines of the invention will extrude or secrete the heterologous protein along with, or in place of, egg white protein. The avian oviduct tumor cell lines can be assessed for the ability to express heterologous proteins using a variety of art-recognized techniques. Expression of the heterologous protein can be driven by either oviduct-specific or non-specific promoters. The expressed protein can be detected, for example, by ELISA or bioactivity assay. Such heterologous proteins can be any expressible protein and may include, for example, therapeutic proteins such as cytokines, growth factors, enzymes, structural proteins, immunoglobulins, granulocyte-colony stimulating factor, or any other polypeptide of interest that is capable of being expressed by an avian cell or tissue. In one embodiment, the heterologous protein is mammalian, for example, a human protein or is derived from or is a portion of a mammalian, or human protein.

Expression of heterologous proteins may be assessed by any of a wide variety of well known methods for detecting expression of a transcribed nucleic acid or polypeptide. Nonlimiting examples of such methods include immunological methods for detection of secreted, cell-surface, cytoplasmic, or nuclear polypeptides, protein purification methods, protein function or activity assays, nucleic acid hybridization methods, nucleic acid reverse transcription methods, and nucleic acid amplification methods.

In one embodiment, expression of the protein is assessed using an antibody, for example a radio-labeled, chromophore-labeled, fluorophore-labeled, or enzyme-labeled antibody, an antibody derivative, such as an antibody conjugated with a substrate or with the protein or ligand of a protein-ligand pair, for example biotin-streptavidin, or an antibody fragment, for example a single-chain antibody, an isolated antibody hypervariable domain, which binds specifically with a polypeptide or fragment thereof, including a polypeptide which has undergone all or a portion of its normal post-translational modification.

In another embodiment, expression of the protein is assessed by preparing mRNA/cDNA (i.e. a transcribed polynucleotide) from cells, and by hybridizing the mRNA/cDNA with a reference polynucleotide which is a complement of a polypeptide nucleic acid, or a fragment thereof. cDNA can, optionally, be amplified using any of a variety of polymerase chain reaction methods prior to hybridization with the reference polynucleotide. Expression of one or more proteins can likewise be detected using quantitative PCR to assess the level of expression of the protein(s).

The invention provides methods for producing multimeric proteins, for example, immunoglobulins, such as antibodies, and antigen binding fragments thereof.

In one embodiment of the present invention, the multimeric protein is an immunoglobulin, wherein the first and second heterologous polypeptides are an immunoglobulin heavy and light chains respectively. Illustrative examples of this and other aspects and embodiments of the present invention for the production of heterologous multimeric polypeptides in avian cells are fully disclosed in U.S. patent application Ser. No. 09/877,374, filed Jun. 8, 2001, published as US-2002-0108132-A1 on Aug. 8, 2002, and U.S. patent application Ser. No. 10/251,364, filed Sep. 18, 2002, each of which are incorporated herein by reference in their entirety. In one embodiment of the present invention, therefore, the multimeric protein is an immunoglobulin wherein the first and second heterologous polypeptides are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by the transcriptional unit of an expression vector may also be an immunoglobulin light chain polypeptide comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In certain embodiments, the antibodies are human or humanized.

In other embodiments of the present invention, the immunoglobulin polypeptide encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of an heterologous protein capable of forming an antibody suitable for selectively binding an antigen including producing a transgenic avian incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In an embodiment of this method of the present invention, the isolated heterologous protein is an antibody capable of selectively binding to an antigen. In one embodiment, the antibody may be generated by combining at least one immunoglobulin heavy chain variable region and at least one immunoglobulin light chain variable region, for example, cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin polypeptide. The method may include combining certain isolated heterologous immunoglobulin polypeptides, thereby producing an antibody capable of selectively binding to an antigen. In this embodiment, two individual transgenic avians may be generated wherein one transgenic produces serum or eggs having an immunoglobulin heavy chain variable region, or a polypeptide comprising such, expressed therein. A second transgenic animal, having a second transgene, produces serum or eggs having an immunoglobulin light chain variable region, or a polypeptide comprising such, expressed therein. The polypeptides may be isolated from their respective sera and eggs and combined in vitro to generate a binding site capable of binding an antigen.

The present invention is useful for the production of many biological products such as, pharmaceutical compositions. For example, the present invention can be useful for the production of biological molecules such as hormones including cytokines (i.e., secreted polypeptides that affect a function of cells and modulates an interaction between cells in an immune, inflammatory or hematopoietic response), antibodies and other useful pharmaceutical molecules which include polypeptides. Cytokines includes, but are not limited to, monokines and lymphokines. Examples of cytokines include, but are not limited to, interferon α2b, Interleukin-1 (IL-1), Interleukin-6 (IL-6), Interleukin-8 (IL-8), Tumor Necrosis Factor-α (TNF-α.) and Tumor Necrosis Factor β (TNF-β), antibodies such as polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, F(Ab')$_2$ fragments, fragments produced by a FAb expression library, anti-idiotypic (anti-Id) antibodies, and epitope-binding fragments thereof. Also contemplated is the production of antibody fusion proteins, for example, Fc fusion proteins in accordance with the present methods. The methods of the present invention can also be useful for producing immunoglobulin polypeptides which are constituent polypeptides of an antibody or a polypeptide derived therefrom. An "immunological polypeptide" may be, but is not limited to, an immunological heavy or light chain and may include a variable region, a diversity region, joining region and a constant region or any combination, variant or truncated form thereof. Immunological polypeptides also include single-chain antibodies comprised of, but not limited to, an immunoglobulin heavy chain variable region, an immunoglobulin light chain variable region and optionally a peptide linker.

Examples of certain antibodies that can be produced in methods of the invention may include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-$\alpha V\beta 3$ integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-$\alpha$ antibody (CAT/BASF); CDP870 is a humanized anti-TNF-$\alpha$ Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-$\alpha$ IgG4 antibody (Celltech); LDP-02 is a humanized anti-$\alpha 4\beta 7$ antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta_2$ antibody (Cambridge Ab Tech).

Other possible pharmaceutical compositions contemplated for production in accordance with the present invention, but are not limited to, albumin, $\alpha$-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Other pharmaceutical compositions which may be produced as disclosed herein are disclosed in, for example, patents or pending patent applications which have incorporated herein by reference elsewhere in the application.

Heterologous protein(s) produced from avian oviduct tumor cells in accordance with the present invention can be isolated from the medium in which the tumor cells are cultured using any of a variety of art-recognized techniques. Dialysis of the medium against dilute buffer or a superabsorbant material, followed by lyophilization, can be employed to remove the bulk of the low molecular weight components of the medium and to concentrate the heterologous protein. Alternatively, ultrafiltration or precipitation by saturation with salts such as sodium or ammonium sulfate can be used.

Once obtained in concentrated form, any standard technique, such as preparative disc gel electrophoresis, ion-exchange chromatography, gel filtration, size separation chromatography, isoelectric focusing and the like may be used to purify, isolate, and/or to identify the heterologous protein. Those skilled in the art may also readily devise affinity chromatographic means of heterologous protein purification, especially for those instances in which a binding partner of the heterologous protein is known, for example, antibodies.

Those skilled in the art will recognize, or be able to ascertain using no more than routine experimentation, many equivalents to the specific embodiments of the invention described herein. Such equivalents are intended to be encompassed by the following claims.

The present invention is further illustrated by the following examples, which are provided by way of illustration and should not be construed to limit the invention. The contents of all references, published patents and patents cited throughout the present application are hereby incorporated by reference in their entireties.

Example 1

Production of an Immortal Cell Line from Avian Oviduct Tissue

Epithelial adenoma tumors are isolated from a chicken oviduct and are finely minced into 1 to 2 mm pieces which are incubated in F12 medium with 0.8 mg/ml collagenase. The tissue is shaken at 37° C. for 30 minutes and triturated to generate cell clumps consisting of approximately 100 to 1000 cells. The clumps of cells are separated from red blood cells and cellular debris which is discarded. The clumps are suspended in pre-warmed F12 media, supplemented with 0.8 mg/ml collagenase and 1.0 mg/ml dispase, and incubated at 37° C. with shaking. Cell clumps are triturated every ten minutes to generate clumps consisting of about 5 to 100 cells. The cells are pelleted with low speed centrifugation and the resultant pellet is suspended in ice cold F12 which is filtered through a single layer of sterile surgical gauze tape to remove larger cell clumps. The cells are washed twice with ice cold F12, pelleted and resuspended in DMEM 15% FCS growth medium at an $OD_{600}$ of approximately 1.0.

The cells are grown in growth media at 2% $CO_2$ and 42° C. until the culture reaches confluency or until the diameter of cell clumps reach approximately one millimeter. Cell clumps and monolayers are subsequently treated with basal salts media which includes 0.8 mg/ml collagenase and 1.0 mg/ml dispase to produce a single cell suspension. Cells are pelleted and washed twice with basal salt media. After final wash, the cell pellet is suspended in growth media at a cell density of $1\times10^4$-$10\times10^6$ cells per milliliter.

Single cells are plated in each well of 96 well plate and incubated in growth media. Immortal cell lines are identified which produce ovalbumin as determined by ELISA. Cells that express ovalbumin are passaged as needed to maintain viability. Each cell line is passaged a minimum of 20 times.

Example 2

Production of an Immortal Cell Line from Avian Oviduct Tissue of a Transgenic Avian and Production of Heterologous Protein Transgenic chickens which produce eggs with interferon present in the egg white are disclosed in U.S. Pat. No. 6,730, 822. An interferon producing transgenic chicken is matured to five years of age. Oviduct tissue is removed from the chicken and several tumors are isolated. An immortal cell line is obtained from the tumors as described in Example 1.

Growth medium in which the immortal ovalbumin producing cell lines are passaged tests positive for interferon.

Example 3

Production of an Immortal Cell Line from Avian Tubular Gland Cells

Freshly harvested chicken oviduct tissue is isolated from a healthy 40 week old chicken. The tissue is finely minced into small pieces approximately 1 mm in diameter. The tissue is shaken at 42° C. for 20 min and triturated to generate clumps each consisting of about 100 to 1000 cells. The clumps of cells are separated from red blood cells and cellular debris which is discarded and are then suspended in pre-warmed McCoy's 5A medium, supplemented with 0.8 mg/ml collagenase and 1.0 mg/ml dispase, and incubated at 42° C. with shaking. The cell clumps are triturated every ten minutes to generate clumps consisting of about 5 to 100 cells. The cells are then collected by low speed centrifugation. The resultant pellet is suspended in ice cold McCoy's 5A medium and filtered through a single layer of sterile surgical gauze tape to remove large clumps. The cells are then washed 2 times in McCoy's 5A medium.

Cells are centrifuged, counted, and resuspended in serum-free RPMI medium 1640 containing 0.4 mg/ml Aroclor 1254-induced S9 rat liver extracts (Moltox, Boone, N.C.), 0.23 mM NADP, 0.28 mM glucose 6-phosphate, 0.45 mM $MgCl_2$, 0.45 mM KCl, and 200 mM Tris·HCl (pH 7.5) plus 50 uM N-methyl-N'-nitro-N-nitrosoguanidine (MNNG).

The cells are treated for 2 hours at 42° C. After treatment, the cells are resuspended in complete McCoy's 5A medium and reseeded. MNNG-resistant cell lines are established by two successive treatments with 5 uM MNNG and 25 uM $O^6$-benzylguanine. Each round of treatment is performed after cells surviving the prior round of treatment have recovered exponential growth. Single-cell clones are obtained by limiting dilution. Each clone is grown to confluency in a well of a six well plate. Each cell line is passaged a minimum of 20 times.

Example 4

Transformation of an Avian Tubular Gland Cell Immortal Cell Line and Production of Heterologous Protein An immortal cell line of Example 1 and Example 3 is transformed with an OMC24-attB-IRES-G-CSF vector with a neomycin resistance coding sequence inserted downstream of the ovomucoid transcription initiation start site such that both the G-CSF and neomycin resistance are expressed. OMC24-attB-IRES-G-CSF is disclosed in U.S. patent application Ser. No. 10/940,315, filed Sep. 14, 2004 and U.S. patent application Ser. No. 10/856,218, filed May 28, 2004. The disclosure of each of these two patent applications is incorporated herein in its entirety by reference.

OMC24-attB-IRES-G-CSF-Neo is transfected into actively growing cell lines produced as described in Example 1 and Example 3. For each cell line, 0.2 ml of cells, which have been washed in OptiMem medium, and 0.6 ml of OptiMem medium plus 10 nm estrogen, 100 nm corticosterone and 1 um insulin (OptiMem) are added to each of six wells in a six well multiwell plate.

For each transfection, 5 ul of Dmrie C (Invitrogen, Inc.) and 95 ul of OptiMem is added to a polycarbonate tube. Approximately 20 ug of the OMC24-attB-IRES-G-CSF-Neo vector in 100 ul of OptiMen is mixed into the Dmrie solution by pipetting. The DNA-lipid mixture is let to stand for about 15 min at room temperature in the hood.

200 ul of the lipid/DNA/OptiMem mix is added to the 0.8 mls of cells in each well for a total of 1 ml volume. Incubate at 42° C., 5% $CO_2$ for at least 5 to 6 hours.

2 mls of 15% FCS DMEM plus 10 nm estrogen, 100 nm corticosterone and 1 um insulin high glucose with no phenol red with 2× neomycin is added to the transfection medium. The cells are incubated for 24 hours followed by a change medium to fresh 10% FCS DMEM hi glucose plus neomycin with no phenol red followed by 24 hours of incubation. The cells are diluted and grown for an additional 24 hour at which time individual colonies are picked, transferred to individual wells of a six well plate and grown to confluency. For each cell line which is passaged a minimum of 20 times, the growth medium tests positive for G-CSF.

While this invention has been described with respect to various specific examples and embodiments, it is to be understood that the invention is not limited thereto and that it can be variously practiced with the scope of the following claims.

What is claimed is:

1. A method comprising:
   obtaining a cell from a tumor present in a tubular gland of a chicken oviduct; and culturing the obtained cell in cell culture medium.

2. The method of claim 1 wherein the tumor is an epithelial adenoma.

3. The method of claim 1 wherein the chicken is aged to at least about five years.

4. A method comprising,
   i) obtaining at least one cell from tumorous tubular gland cells in an oviduct of a transgenic chicken, wherein the obtained at least one tumorous tubular gland cell of the transgenic chicken contains in the transgenic chicken genome a nucleotide sequence that is operably linked to a promoter and that encodes an exogenous protein;
   ii) culturing the obtained at least one tumorous tubular gland in cell culture medium cell to express the exogenous protein in cell culture medium; and
   iii) isolating the exogenous protein.

5. The method of claim 4 wherein the promoter is a heterologous promoter.

6. The method of claim 4 wherein the exogenous protein is selected from the group consisting of an antibody, a cytokine, a fusion protein, a growth factor, an enzyme, a structural protein, an interferon, a granulocyte-colony stimulating factor and an erythropoietin.

7. A method comprising,
i) obtaining at least one cell from tumorous tubular gland cells in a chicken oviduct;
ii) culturing the obtained at least one cell in cell culture medium;
iii) introducing into the cultured cell(s) and progeny therein a nucleotide sequence operably linked to a promoter, wherein the nucleotide sequence comprises a coding sequence encoding a heterologous protein wherein the nucleotide sequence is expressed to produce the heterologous protein; and
iv) isolating the heterologous protein.

8. The method of claim 7 wherein the promoter is selected from the group consisting of a cytomegalovirus (CMV) promoter, and a rous-sarcoma virus (RSV) promoter.

9. The method of claim 7 wherein the heterologous protein is a therapeutic protein.

10. The method of claim 7, wherein the nucleotide sequence further comprises a sequence encoding a selectable marker operably linked to an expression control sequence and wherein the method further comprises selecting for tumor cells that express the marker.

11. The method of claim 7 wherein the chicken is at least about five years of age.

12. The method of claim 7 wherein the tumorous tubular gland cells are epithelial adenoma.

13. The method of claim 7 wherein the heterologous protein is selected from the group consisting of an antibody, a cytokine, a fusion protein, a growth factor, an enzyme, a structural protein, an interferon, a granulocyte-colony stimulating factor, and an erythropoietin.

* * * * *